United States Patent [19]
Hei

[11] Patent Number: 6,024,986
[45] Date of Patent: Feb. 15, 2000

[54] METHOD OF PROTECTING GROWING PLANTS FROM THE EFFECTS OF PLANT PATHOGENS

[75] Inventor: Robert D.P. Hei, Baldwin, Wis.

[73] Assignee: Ecolab Inc., St. Paul, Minn.

[21] Appl. No.: 09/317,320

[22] Filed: May 24, 1999

[51] Int. Cl.[7] ............... A01N 59/00; A01N 37/02; A01N 37/06; A01N 37/16

[52] U.S. Cl. ............... 424/616; 424/DIG. 8; 514/557; 514/558; 514/559; 514/560; 504/116; 504/125; 504/320

[58] Field of Search ............... 424/616, DIG. 8; 514/557, 558, 559, 560; 504/116, 125, 320

[56] References Cited

U.S. PATENT DOCUMENTS

| | | | |
|---|---|---|---|
| 2,512,640 | 6/1950 | Greenspan et al. | 514/557 |
| 2,833,813 | 5/1958 | Wallace | 562/5 |
| 3,442,937 | 5/1969 | Sennewald et al. | 562/3 |
| 4,051,059 | 9/1977 | Bowing et al. | 252/186.23 |
| 4,649,113 | 3/1987 | Gould | 435/165 |
| 5,122,538 | 6/1992 | Lokkesmoe et al. | 514/557 |
| 5,139,788 | 8/1992 | Schmidt | 424/616 |
| 5,162,052 | 11/1992 | Hoffmann et al. | 47/8 |
| 5,168,655 | 12/1992 | Davidson et al. | 47/62 N |
| 5,200,189 | 4/1993 | Oakes et al. | 514/557 |
| 5,314,687 | 5/1994 | Oakes et al. | 514/557 |
| 5,395,530 | 3/1995 | Robertson et al. | 210/632 |
| 5,409,713 | 4/1995 | Lokkesmoe et al. | 424/616 |
| 5,436,008 | 7/1995 | Richter et al. | 424/405 |
| 5,437,868 | 8/1995 | Oakes et al. | 424/405 |
| 5,472,619 | 12/1995 | Holzhauer et al. | 210/721 |
| 5,489,434 | 2/1996 | Oakes et al. | 424/405 |
| 5,565,213 | 10/1996 | Nakamori et al. | 424/450 |
| 5,567,444 | 10/1996 | Hei et al. | 424/616 |
| 5,597,791 | 1/1997 | Richards et al. | 510/372 |
| 5,647,997 | 7/1997 | Holzhauer et al. | 210/721 |
| 5,723,406 | 3/1998 | Larose et al. | 504/114 |
| 5,773,696 | 6/1998 | Liang et al. | 800/205 |
| 5,858,443 | 1/1999 | Hei et al. | 426/506 |

FOREIGN PATENT DOCUMENTS

| | | |
|---|---|---|
| 9 300 538 | 11/1994 | Denmark . |
| 0 035 800 A2 | 9/1981 | European Pat. Off. . |
| 0 233 731 A2 | 8/1987 | European Pat. Off. . |
| 0 242 990 A2 | 10/1987 | European Pat. Off. . |
| 0 361 955 A2 | 4/1990 | European Pat. Off. . |
| 30 03 875 A1 | 8/1981 | Germany . |
| 0523092 | 2/1993 | Japan . |
| 7-31210 | 2/1995 | Japan . |
| 7-258005 | 10/1995 | Japan . |
| 2 187 958 | 9/1987 | United Kingdom . |
| 2 257 630 | 1/1993 | United Kingdom . |
| WO 94/06294 | 3/1994 | WIPO . |
| WO 95/28840 | 11/1995 | WIPO . |
| WO 97/08100 | 3/1997 | WIPO . |

OTHER PUBLICATIONS

Derwent Abstract, Accession No. 1993–079367, Abstracting JP 05–23092 (1993).
CABA Abstract, Accession No. 83:12115 (1983).
CABA Abstract, Accession No. 88: 10112 (1987).

*Primary Examiner*—John Pak
*Attorney, Agent, or Firm*—Merchant & Gould P.C.

[57] ABSTRACT

The direct introduction or injection of peroxy compounds into a transpiration layer in a plant structure found inside the protective layer, bark or husk of a growing plant is described as an effective method in treating plant disease and can achieve levels of protection unavailable in the simple application of the materials to the leaf, stem, root or plant environment including air or soil.

22 Claims, 10 Drawing Sheets

Fig. 1 *Erwinia amylovora*
Untreated Control on NW Greening Apple
(5 months after exposure)

Fig. 2   *Erwinia amylovora*
Peracid Injected Sungold Apricot
(7 months after exposure)

Fig. 3  *Erwinia amylovora*
Peracid Injected Moongold Apricot
(7 months after exposure)

Fig. 4  _Erwinia amylovora_
Peracid Injected Chestnut Crab
(7 months after exposure)

Fig. 5   *Erwinia amylovora*
Peracid Injected Dolgo Crab
(7 months after exposure)

Fig. 6

Erwinia amylovora
Peracid Treated Summercrisp Pear
(7 months after exposure)

Fig. 7     *Erwinia amylovora*
Peracid Injected Red Regent Apple
(7 months after exposure)

Fig. 8

*Erwinia amylovora*
Peracid Injected Red Baron Apple
(17 months after exposure)

Fig. 9 *Erwinia amylovora*
Peracid Injected Summercrisp Pear
(17 months after exposure)

Fig. 10  *Erwinia amylovora*
Peracid Injected Luscious Pear
(17 months after exposure)

METHOD OF PROTECTING GROWING PLANTS FROM THE EFFECTS OF PLANT PATHOGENS

FIELD OF THE INVENTION

The invention relates to methods of treating growing plants for the purpose of protecting the plant from the damaging effect of infective microorganisms including, for example, fungi, bacteria, yeasts, and the like.

BACKGROUND OF THE INVENTION

Diseases in growing plants are well known. Such diseases have resulted in substantial food and economic loss to farmers for many years. Farmers often combat such diseases using harsh techniques including sacrificing one or more infected plants by burning, cutting or other destructive measures. In the past, diseases of growing plants have been treated using a variety of chemical materials including toxic metals, organic fungicides or herbicides. These compositions have had some effect in alleviating plant disease. Many of these materials are contacted with the plant through fogging, spraying or injection of the material into the soil surrounding the plant. Such treatments typically tend to concentrate the active material on the surface layers of the fruit, leaf, stem or root in the plant with an eye towards preventing the introduction of infective microorganisms through the protective outer layers of the plant surface. The outer layers of fruit, leaf, stem and root often have protective measures that attempt to prevent the attack by fungi and other active microorganisms on plant tissues. Such chemical treatments have had some success, however, the use of toxic metals, organic fungicides and other toxic materials are dangerous to the user and often pose an environmental challenge and can cause undesirable effects in killing other beneficial organisms.

Peroxy compounds; notably, peroxy acid/hydrogen peroxide compositions, are well known in the prior art as sanitizing materials. Particularly, the Grosse Bowing patents, U.S. Pat. Nos. 4,051,058 and 4,051,059, disclose basic formulation materials in stabilizing peroxy acetic acid/hydrogen peroxide compositions using sulfonate or phosphonate stabilizing agents. The prior art regarding the use of these materials has developed actively. Also, the Grosse Bowing patents describe stabilized peracid materials using sulfonate and phosphonate stabilizing agents. Sennewald et al., U.S. Pat. No. 3,442,937, describes quinolin polyphosphate or urea stabilized peracid solutions. Malone et al, U.S. Pat. No. 5,565,213, describe stabilization of water containing high concentration of sugar materials. Richards et al, U.S. Pat. No. 5,597,791, describe gelled or colloidal peracid treatment compositions. These materials have applications as surface cleaners, detergent, bleaches, automatic dishwashing formulations and similar.

Lokkesmoe et al., U.S. Pat. No. 5,122,538, describe a specialized peroxy acid generator apparatus used to make percarboxylic acid materials. Schmidt, U.S. Pat. No. 5,139,788, describes an antimicrobial composition. Oakes, U.S. Pat. No. 5,200,189, describes peroxy acid antimicrobial compositions. Lokkesmoe, U.S. Pat. No. 5,409,713, describes a process for inhibiting microbial growth in aqueous transport systems contaminated with substantial proportions of food waste, dirt and other agricultural by-products. Richter, U.S. Pat. No. 5,436,008, describes sanitizing compositions. Hei et al, U.S. Pat. No. 5,567,444, describe potentiated aqueous ozone containing cleaning and sanitizing compositions using ozone in combination with materials that enhance cleaning properties. Hei, U.S. Pat. No. 5,858,443, describes methods for effective microbial control in reducing slime in hard surfaces common in food processing equipment using in line ozone injection. Holzhauer et al., U.S. Pat. Nos. 5,472,619 and 5,647,997 describe the use of peracetic acid materials in purification of highly contaminated waste waters. Such waste waters are contaminated with substantial proportions of food waste which are typically skimmed prior to treatment. These food contaminated wastes are different than waters commonly found in decorative, recreational or sporting loci. Lastly, Robertson et al., U.S. Pat. No. 5,395,530, describe using a combination of a toxic biocide and an enzyme for destroying filamentous bacteria.

Huss et al, PCT WO 97/08100, describe the use of peracetic acid materials to disinfect large quantities of waste water such as waste water containing substantial concentration of food waste, brewery waste, dairy waste, effluent or sludge from municipal sewage works or other contaminated material. Commonly, such peroxy materials are used by contacting soiled or contaminated surfaces with the peracid material for the purpose of substantially reducing harmful populations of microorganisms on the surface. The art recognizes that these peracid materials have substantial utility in killing microorganisms.

Similarly, the art has recognized that hydrogen peroxide, peroxy acid/hydrogen peroxide, peracetic acid/hydrogen peroxide materials can be useful in reducing harm to growing plants by the topical application of such materials on the exterior surfaces of plant, bud, fruit, leaf, stem and root. Representative examples of the known technology in this area include Soyez, PCT WO 95/28840; Goebel et al., EP 35800; Lippert, DK 9300538; Otsuka, JP 7031210; Otsuka, JP 7258005; Langford, EP 242990; Wright et al., PCT WO 94/06294; Larose et al., U.S. Pat. No. 5,723,406; and Hoffman et al., U.S. Pat. No. 5,162,052. This body of art describes that growing plants can be treated with a variety of anti-plant disease agents by applying the agent topically or in a controlled release mode to the surface of the plant leaf, stem or root. We have found that such chemical treatments to the exterior of plant tissue often are insufficient to obtain sufficient protection from plant disease to the growing plant. We believe that the reduced efficacy of these materials is substantially related to the fact that the active components in the hydrogen peroxide, hydrogen peroxide/peroxy compound, hydrogen peroxide peracetic acid compounds are prevented from attacking pathological microorganisms within the plant because they are limited to the surface of the plant by the protective layers of the plant structure. Our testing shows that simple topical application of the materials to plants can often result in the loss of the plant completely and spread of contagion to neighboring plants.

A substantial need exists for methods of treating growing plants, particularly plants having an active transpiration layer that can operate to protect growing plants from the undesirable effects of infective microorganisms.

SUMMARY OF THE INVENTION

We have found that the direct application or injection of an antimicrobial composition directly into a cambium layer of growing plants is surprisingly successful in protecting the plant from the undesirable effects of plant pathogens. In our testing, we have found that the simple topical application of such materials to the exterior of the plant provides little or no protection from plant pathogens while the direct injection of the material into a growing, transpiration layer in the growing plant can have a significantly improved effect in protecting the plant from plant pathogens. Such layers are typically called cambium layers. For the purpose of this patent application cambium layer is typically a layer of relatively delicate meristematic tissue between the inner bark or phloem and the wood or xylem of a growing plant, particularly growing trees. The cambium layer produces new phloem on the outside of the layer and new xylem on the inside of the cambium layer in stems, roots, etc. of growing plants, particularly trees. The cambium originates all secondary growth in plants and forms the annual rings of wood in growing trees. The cambium layer is also an active transpiration layer. The term "transpiration layer" is used for the purpose of the present invention to mean a layer that participates in the transfer of materials either from root to leaf or from leaf to root in the growing processes of the plant structure.

Accordingly, the present invention is a method of protecting a growing plant from plant pathogens including injecting into an active transpiration layer of said plant a dilute aqueous solution having an effective amount of a water soluble peroxygen compound or mixtures thereof.

Another aspect of the present invention is a method of treating a growing plant having an active transpiration layer to reduce the effect of plant pathogens on or in the growing plant, the method including the steps of forming a passageway into the cambium layer of a growing plant, and applying through the passageway an effective plant treating amount of a water soluble antimicrobial composition for sufficient period of time to reduce the undesirable effects of a plant pathogen on the plant life.

BRIEF DESCRIPTION OF THE DRAWINGS

FIG. 1 is a photograph of a NW Greening Apple tree used as an untreated control, seen five months after exposure to *Erwinia amylovora*.

FIG. 2 is a photograph of a peroxycarboxylic acid injected Sungold Apricot seen seven months after exposure to *Erwinia amylovora*.

FIG. 3 is a photograph of a peroxycarboxylic acid injected Moongold Apricot seen seven months after exposure to *Erwinia amylovora*.

FIG. 4 is a photograph of a peroxycarboxylic acid injected Chestnut Crab seen seven months after exposure to *Erwinia amylovora*.

FIG. 5 is a photograph of a peroxycarboxylic acid injected Dolgo Crab seen seven months after exposure to *Erwinia amylovora*.

FIG. 6 is a photograph of a peroxycarboxylic acid injected Summercrisp Pear seen seven months after exposure to *Erwinia amylovora*.

FIG. 7 is a photograph of a peroxycarboxylic acid injected Red Regent Apple seen seven months after exposure to *Erwinia amylovora*.

FIG. 8 is a photograph of a peroxycarboxylic acid injected Red Baron Apple seen seventeen months after exposure to *Erwinia amylovora*.

FIG. 9 is a photograph of a peroxycarboxylic acid injected Summercrisp Pear seen seventeen months after exposure to *Erwinia amylovora*.

FIG. 10 is a photograph of a peroxycarboxylic acid injected Luscious Pear seen seventeen months after exposure to *Erwinia amylovora*.

DETAILED DESCRIPTION OF THE INVENTION

The invention involves injecting a peroxygen compound into an affected plant or tree. Preferably, the peroxygen compound is hydrogen peroxide, a peroxycarboxylic acid, or an equilibrium combination of hydrogen peroxide, a peroxycarboxylic acid and the corresponding carboxylic acid; or an equilibrium combination of hydrogen peroxide, a blend of peroxycarboxylic acids and their corresponding carboxylic acids. The concentrate may also include other ingredients such as stabilizers, couplers, etc. as mentioned below.

Among the above constituents in the antimicrobial concentrate composition the invention includes a carboxylic acid. Generally, carboxylic acids have the formula R—COOH wherein the R may represent any number of different groups including aliphatic groups, alicyclic groups, aromatic groups, heterocyclic groups, all of which may be saturated or unsaturated as well as substituted or unsubstituted. Carboxylic acids also occur having one, two, three, or more carboxyl groups.

Carboxylic acids have a tendency to acidify aqueous compositions. In acid systems, they may also exhibit antimicrobial activity.

The peroxycarboxylic acid constituent within the present composition functions as the antimicrobial agent. Moreover, the peroxycarboxylic acid constituent within the invention as well as the parent carboxylic acid maintain the composition at an acidic pH.

Peroxycarboxylic acids generally have the formula $R(CO_3H)_{n'}$ where R may represent any number of different groups including aliphatic groups, alicyclic groups, aromatic groups, heterocyclic groups, all of which may be saturated or unsaturated as well as substituted or unsubstituted. Thus, R may be, for example, an alkyl, arylalkyl, cycloalkyl, aromatic or heterocyclic group, and n is one, two, or three, and named by prefixing the parent acid with per or peroxy.

While peroxycarboxylic acids are less chemically stable than their corresponding carboxylic acids, their stability generally increases with increasing molecular weight. Decomposition of these acids may generally proceed by free radical and nonradical paths, by photodecomposition or radical-induced decomposition, by hydrolysis or dissociation or by the action of metal ions or complexes. Peroxycarboxylic acids may be made by the direct, acid catalyzed equilibrium action of 10–98 wt. % hydrogen peroxide with the carboxylic acid, by autoxidation or perhydrolysis of aldehydes, or from carboxylic acid halides, or carboxylic anhydrides with hydrogen, sodium peroxide, or other in-situ sources of hydrogen peroxide.

Peroxycarboxylic acids useful in this invention include $C_2$–$C_{12}$ peroxycarboxylic acids such as, for example, peracetic acid, perpropionic acid, perbutyric acid, perhexanoic acid, perheptanoic acid, peroctanoic acid, pernonanoic acid, perdecanoic acid, perbenzoic acid, perglycolic acid, perglutaric acid, persuccinic acid, perlactic acid, percitric acid, perlauric acid, peradipic acid, permalic acid, perfumaric acid, pertartaric acid or mixtures thereof. These peroxycarboxylic acids have been found to provide good antimicrobial action with good stability in aqueous solutions.

Preferably, the peroxycarboxylic acid used is peroxyacetic acid or, alternatively, includes a mixture of a $C_2$–$C_4$ peroxycarboxylic acid and a $C_5$–$C_{12}$ aliphatic peroxycarboxylic acid. Another preferred embodiment includes a mixture of a $C_2$–$C_4$ peroxycarboxylic acid and a $C_8$–$C_{12}$ aliphatic peroxycarboxylic acid. More preferably, the peroxygen compound is a mixture of peroxyacetic acid and peroxyoctanoic acid.

Generally, the concentration of peroxycarboxylic acid(s) within the composition used in the process of the invention ranges from about 0.1 weight percent to about 40 weight percent, preferably from about 2 weight percent to about 25 weight percent, and most preferably from about 4 weight percent to about 20 weight percent.

Preferably, upon dilution of the concentrate, the aqueous solution used in the invention contains at least about 10 parts per million (ppm) of a peroxygen compound or mixtures thereof. More preferably, the aqueous solution includes at least about 100 parts per million (ppm) of a peroxygen compound or mixtures thereof, and most preferably, the aqueous solution includes at least about 400 parts per million (ppm).

For mixed peracid systems the aqueous solution includes at least about 10 parts per million (ppm) of a $C_2$–$C_4$ peroxycarboxylic acid; and at least about 1 part per million (ppm) of a $C_5$–$C_{12}$ aliphatic peroxycarboxylic acid. More preferably, the aqueous solution includes at least about 75 parts per million (ppm) of a $C_2$–$C_4$ peroxycarboxylic acid; and at least about 5 parts per million (ppm) of a $C_5$–$C_{12}$ aliphatic peroxycarboxylic acid; and most preferably, the aqueous solution includes at least about 250 parts per million (ppm) of a $C_2$–$C_4$ peroxycarboxylic acid; and at least about 25 parts per million (ppm) of a $C_5$–$C_{12}$ aliphatic peroxycarboxylic acid.

In a preferred mode, the antimicrobial concentrate composition of the invention uses peracetic acid. Peracetic acid is a peroxycarboxylic acid having the formula:

$CH_3COOOH.$

Generally, peracetic acid is a liquid having an acrid odor at higher concentrations and is freely soluble in water, alcohol, ether, and sulfuric acid. Peracetic acid may be prepared through any number of means known to those of skill in the art including preparation from acetaldehyde and oxygen in the presence of cobalt acetate. A 50% solution of peracetic acid may be obtained by combining acetic anhydride, hydrogen peroxide and sulfuric acid. Other methods of formulation of peracetic acid include those disclosed in U.S. Pat. No. 2,833,813, which is incorporated herein by reference.

Other methods of formulation of peroxycarboxylic acids within the present invention include those described in U.S. Pat. Nos. 4,051,058, 4,051,059, 5,200,189, 5,314,687 and 5,437,868, which are incorporated herein by reference.

Hydrogen Peroxide

The antimicrobial concentrate composition of the invention may also comprise a hydrogen peroxide constituent. Hydrogen peroxide in combination with the peroxycarboxylic acid provides a surprising level of antimicrobial action against microorganisms. An advantage of hydrogen peroxide is the food compatibility of this composition upon use and decomposition. For example, combinations of peracetic acid and hydrogen peroxide result in acetic acid, water, and oxygen upon decomposition; all of which are food product compatible.

Hydrogen peroxide ($H_2O_2$), has a molecular weight of 34.014 and it is a weakly acidic, clear, colorless liquid. The four atoms are covalently bonded in a non-polar H—O—O—H structure. Generally, hydrogen peroxide has a melting point of –0.41° C., a boiling point of 150.2° C., a density at 25° C. of 1.4425 grams per cm$^3$, and a viscosity of 1.245 centipoise at 20° C.

Generally, the concentration of hydrogen peroxide within the composition used in the process of the invention ranges from about 0.1 weight percent to about 70 weight percent, preferably from about 3 weight percent to about 50 weight percent, and most preferably from about 5 weight percent to about 25 weight percent.

These concentrations of hydrogen peroxide may be increased or decreased while still remaining within the scope of the invention.

Other Components

Various optional materials may be added to the composition of the invention to help solubilize the fatty acids, restrict or enhance the formation of foam, to control hard water, to stabilize the composition, or to further enhance the antimicrobial activity of the composition.

The composition of the invention can contain a surfactant hydrotrope coupling agent or solubilizer that permits blending short chain perfatty acids in aqueous liquids. Functionally speaking, the suitable couplers which can be employed are non-toxic and retain the fatty acid and the perfatty acid in aqueous solution throughout the temperature range and concentration to which a concentrate or any use solution is exposed.

Any hydrotrope coupler may be used provided it does not react with the other components of the composition or negatively affect the antimicrobial properties of the composition. Representative classes of hydrotropic coupling agents or solubilizers which can be employed include anionic surfactants such as alkyl sulfates and alkane sulfonates, linear alkyl benzene or naphthalene sulfonates, secondary alkane sulfonates, alkyl ether sulfates or sulfonates, alkyl phosphates or phosphonates, dialkyl sulfosuccinic acid esters, sugar esters (e.g., sorbitan esters), amine oxides (mono-, di-, or tri-alkyl) and $C_8$–$C_{10}$ alkyl glucosides. Preferred coupling agents for use in the present invention include n-octanesulfonate, available as NAS 8D from Ecolab, n-octyl dimethylamine oxide, and the commonly available aromatic sulfonates such as the alkyl benzene sulfonates (e.g. xylene sulfonates) or naphthalene sulfonates.

Some of the above hydrotropic coupling agents independently exhibit antimicrobial activity at low pH. This adds to the efficacy of the present invention, but is not the primary criterion used in selecting an appropriate coupling agent. Since it is the presence of perfatty acid in the protonated neutral state which provides biocidal activity, the coupling agent should be selected not for its independent antimicrobial activity but for its ability to provide effective interaction between the substantially insoluble perfatty acids described herein and the microorganisms which the present compositions control.

The hydrotrope coupling agent can make up about 0 to 40 wt. %, preferably about 3 to 20 wt. %, and most preferably about 5 to 12 wt. % of the concentrate composition.

Compounds such as mono, di and trialkyl phosphate esters may be added to the composition to suppress foam. Such phosphate esters would generally be produced from aliphatic linear alcohols, there being from 8 to 12 carbon atoms in the aliphatic portions of the alkyl phosphate esters. Alkyl phosphate esters possess some antimicrobial activity in their own right under the conditions of the present invention. This antimicrobial activity also tends to add to the overall antimicrobial activity of the present compositions even though the phosphate esters may be added for other reasons. Furthermore, the addition of nonionic surfactants would tend to reduce foam formation herein. Such materials tend to enhance performance of the other components of the composition, particularly useful nonionic surfactant for use as a defoamer is nonylphenol having an average of 12 moles of ethylene oxide condensed thereon, it being encapped with a hydrophobic portion comprising an average of 30 moles of propylene oxide.

Chelating agents can be added to the composition of the invention to enhance biological activity and stability of the peroxyacids. For example, 1-hydroxyethylidene-1, 1-diphosphonic acid commercially available from the Monsanto Company under the designation "DEQUEST" has been found to be effective. Chelating agents can be added to the present composition to control or sequester hardness ions such as calcium and magnesium. In this manner both detergency and sanitization capability can be enhanced.

Other materials which are sufficiently stable at the low pH contemplated by the present composition may be added to the composition to impart desirable qualities depending upon the intended ultimate use. For example, phosphoric acid ($H_3PO_4$) can be added to the composition of the invention. Additional compounds can be added to the concentrate (and thus ultimately to the use solution) to change its color or odor, to adjust its viscosity, to enhance its thermal (i.e., freeze-thaw) stability or to provide other qualities which tend to make it more marketable.

The composition of the invention can include a single peroxy acid, preferably peroxyacetic acid. In this instance, the peroxy acid can be premade, or can be made by combining the appropriate carboxylic acid with hydrogen peroxide. The equilibrium mixture will include the carboxylic acid, the corresponding peroxycarboxylic acid, hydrogen peroxide, and may optionally contain minor adjuvants such as couplers and stabilizers.

The composition of the invention can also include a mixture of peroxycarboxylic acids. In this instance, they can be made by simply mixing an effective amount of a $C_8$–$C_{12}$ peroxyacid such as peroxyoctanoic acid with some source of a $C_2$–$C_4$ peroxycarboxylic acid such as peroxyacetic acid. This composition would be formulated with preformed perfatty acid and preformed peroxyacetic acid. A preferred composition of the invention can be made by mixing a $C_2$–$C_4$ carboxylic acid, a $C_8$–$C_{12}$ carboxylic acid, a coupler and a stabilizer and reacting this mixture with hydrogen peroxide. A stable equilibrium mixture is produced containing a $C_2$–$C_4$ peroxycarboxylic acid and a $C_8$–$C_{12}$ peroxyacid by allowing the mixture to stand for from one to seven days at 15° C. to 25° C. As with any aqueous reaction of hydrogen peroxide with a free carboxylic acid, this gives a true equilibrium mixture. In this case, the equilibrium mixture will contain hydrogen peroxide, a $C_2$–$C_4$ peroxycarboxylic acid, a $C_8$–$C_{12}$ carboxylic acid, a $C_2$–$C_4$ peroxycarboxylic acid, a $C_8$–$C_{12}$ peroxyacid, water, and various couplers and stabilizers.

By using the above approach, the composition of the invention can be formulated by merely mixing readily available raw materials, e.g., acetic acid, hydrogen peroxide and fatty acid. By allowing solution time for equilibrium to be obtained, the product containing both of the active biocides is obtained. In varying the ratio of $C_2$–$C_4$ carboxylic acid to $C_8$–$C_{12}$ carboxylic acid, it is easy to vary the ratio of $C_2$–$C_4$ peroxycarboxylic acid to $C_8$–$C_{12}$ peroxyacid.

The table below describes useful, preferred and more preferred formulations:

| Component | Useful | Preferred | More Preferred |
|---|---|---|---|
| peroxycarboxylic acid 1 | 0.1–40 | 2–25 | 4–20 |
| peroxycarboxylic acid 2 | 0–20 | 0–5 | 0–3 |
| hydrogen peroxide | 0–70 | 3–50 | 5–25 |
| carboxylic acid 1 | 0.1–75 | 5–60 | 10–40 |
| carboxylic acid 2 | 0–75 | 0–30 | 0–15 |
| chelating agent | 0–15 | 0–5 | 0–3 |
| solubilizer | 0–40 | 0–20 | 0–12 |
| water | balance | balance | balance |

The table below describes several preferred formulations:

| Component | Weight percent |
|---|---|
| deionized water | 2.4 |
| 1-hydroxyethylidene-1,1-diphosphonic acid | 1.6 |
| acetic acid | 11.2 |
| hydrogen peroxide, 35% | 84.8 |
| deionized water | 3.80 |
| 1-hydroxyethylidene-1,1-diphosphonic acid | 1.50 |
| glacial acetic acid | 43.85 |
| hydrogen peroxide, 35% | 50.85 |
| deionized water | 5.30 |
| glacial acetic acid | 43.85 |
| hydrogen peroxide, 35% | 50.85 |
| deionized water | 26.0 |
| 1-hydroxyethylidene-1,1-diphosphonic acid | 1.5 |
| acetic acid, 100% | 30.0 |
| hydrogen peroxide, 35% | 26.0 |
| NAS-FAL (surfactant) | 12.5 |
| octanoic acid | 4.0 |
| 1-hydroxyethylidene-1,1-diphosphonic acid | 1.0 |
| acetic acid, 100% | 59.0 |
| hydrogen peroxide, 35% | 25.0 |
| octanoic acid | 15.0 |
| 1-hydroxyethylidene-1,1-diphosphonic acid | 1.0 |
| benzoic acid, 100% | 25.0 |
| hydrogen peroxide, 35% | 45.0 |
| octanoic acid | 20.0 |
| NAS-FAL (surfactant) | 9.0 |

Methods

We have found that growing plants can be protected from plant pathogens by injecting into an active transpiration layer of the plant a dilute aqueous solution including an effective amount of a water soluble peroxygen compound or mixtures thereof. Preferably, this is accomplished by forming a passageway into the cambium layer of a growing plant; and applying through the passageway an effective plant treating amount of a water soluble antimicrobial composition for sufficient period of time to reduce the undesirable effects of a plant pathogen on the plant life. Most preferably, this is accomplished by use of a syringe, a hypo shunt, a motorized syringe, or a screw pump and probe, root injection systems, etc., which are capable of penetrating the bark of the plant or tree. Also, one might envision a root feeding system that, over time, would allow for natural root systemic activities of peracid into the transpiration layer.

It is important that the peroxygen solution be injected into the cambium layer, as it is this layer which is actually alive in the tree. Further, injection into this layer will aid in distribution of the solution. It has been found, for example, that liquids injected into the cambium layer can move vertically several inches in less than an hour. It has been found that it is preferable to make multiple injections around the circumference of the affected tree trunk or branch.

As described in the Working Examples below, it has been discovered that the treatment methods described by the invention do not completely prevent tissue damage to the tree or plant. What is important is that these methods prevent girdling of the tree, which is fatal. It has been discovered, however, that at least a portion of the tissue affected by the sub-surface pathogen can recover.

Uses

Fire Blight is a destructive bacterial disease of the Roseacea family which includes—for example—apples (Malus), apricots, plums and cherries (Prunus), hawthorns (Cratageous), mountain ash (Sorbus), and pears (Pyrus). The disease is extremely virulent and readily kills blossoms, shoots, limbs, and often entire trees. Fire Blight is caused by a proficient epiphyte *Erwinia amylovora* which is capable of colonizing and multiplying on the surfaces of plants. Its short, rod-shaped cells have peritrichous flagella that enable it to swim through films of water; especially those existing in plant tissues. The bacterium produces an extra-cellular polysaccharide that embeds millions of cells in a slimy bacterial ooze. Unlike its soft-rotting relatives, *E. amylovora* does not produce extra-cellular pectolytic enzymes. The bacterium can grow epiphytically on leaves, shoots, and blossoms, and it can colonize healthy parenchyma tissues intercellularly without initially causing any apparent disease. However, unlike other fruit-plant pathogens like apple scab, where primary spore inoculum might be dispersed within hours of infection, the bacteria causing fire blight can disperse, colonize, and be redispersed repeatedly for several weeks before bloom when the first infections might occur; i.e., the bacteria are dispersed widely for several weeks to a month or longer before actual inoculation and the first infections occur. Furthermore, it makes little difference whether the plants colonized are susceptible or resistant to fire blight. At moderately warm temperatures in the 65–75° F. range, the bacterium has the potential to double every 20–30 minutes. One bacterium gives rise to 1 trillion cells with just 31 divisions which occur within just 2–3 days. Because blossom infections occur within minutes, even a single wetting event under the right conditions at bloom can increase the number of inoculum sources in an orchard from a few overwintering cankers to several hundred thousand blighted spurs very quickly. Indeed, when conditions are favorable, just spraying water at bloom can incite hundreds of blossom infections per tree. Each new infection provides trillions of new bacterial available for dispersal by wind, water and insects contributing to secondary infection cycles and additional losses that often develop exponentially over time. This, coupled with the speed of infection, explains why incidents of fire blight often appear explosive.

Fire Blight symptoms include blossom and vegetative shoot infections which usually are first noticed when the flowers wilt and turn brown to black. The infection often progresses into the spur, leaving the entire cluster blighted. Often the infection continues into the branch, the branch is girdled, and everything distal to that point wilts. Blighted shoots often show a characteristic "shepherd's crook." The wilted leaves and shoots turn brown to black, taking on a scorched appearance. The advance of the lesion down the shoot into the branch progresses rapidly, leaving the bark sunken and blackened, leading to necrosis of the side branches as it goes. A shoot infection that progresses to a main scaffold branch will likely advance to girdle the branch, killing everything above that point. The rate at which the lesion advances varies widely from one cultivar to another. On some cultivars, for example, a blossom infection normally does not extend beyond the spur, while on others it may quickly advance into 2 and 3 year old branches. The extent of lesion development is dependent on the environment and on the physiological state of the infected tissues. Temperature is the most important environmental factor, 27° C. (80° F.) being optimum. Canker extension is much more rapid on succulent new growth than on older tissues. Infected fruit on these branches may show watersoaked lesions that gradually enlarge, turning brown to black. Droplets of sticky ooze often form on the surface of the fruit. The advance of cankers down the branches and trunk can usually be seen by discoloration of the inner bark tissues well ahead of the externally visible discoloration. The margins of the canker are indefinite at first, but late in the season the margin will become more sharply defined. Bacterial ooze often can be seen emanating from lenticles or small cracks in the bark.

The bacterial pathogen causing Fire Blight overwinters almost exclusively in cankers on limbs infected the previous season. The largest number of cankers and, hence, those most important in contributing inoculum, occur on limbs smaller than 1.5 inches (38 mm) in diameter, especially around cuts made the previous year to remove blighted limbs. The bacteria overwinter near the margins of cankers formed the previous season on twigs, branches and trunks of the trees. The bacterial actually carry over and become active again on only a small proportion of the cankers. They are more likely to overwinter on smooth margined (or indeterminate) cankers than on rough margined (or determinate) cankers. During the early spring as tree growth starts in response to warmer temperatures, the bacteria begin to multiply rapidly and are forced through the surface of the bark (at canker margins and onto the bark surface in droplets of gelatinous yellowish to white ooze up to several weeks before the bloom period. The ooze, containing millions of bacteria, is attractive to many kinds of insects, particularly flies and ants. Insects with small amounts of ooze clinging to their bodies may then visit open blossoms and thus transmit the bacteria to a new site favorable for their multiplication. Once the first few open blossoms are colonized by the bacteria, pollinating insects rapidly move the pathogen to other flowers, initiating more blossom blight. The ooze is also soluble in water, and the bacteria from the oozing cankers can be splashed about by falling or wind-driven rain.

A small amount of blossom infection can explode into a severe situation following a hailstorm. Depending on the cultivar and its stage of development at the time infection occurs, a single blossom or shoot infection can result in the death of an entire limb. If the central leader or trunk of a tree is invaded, a major portion of the tree can be killed in just one season. In general, infections of any type that occur between petal fall and terminal bud set usually lead to the greatest limb and tree loss. In addition, heavily structured trees tend to suffer less severe limb loss than those trained to weaker systems for high productivity. Overall, it is found that an average of between 5 and 15 percent of the trees in an orchard showing symptoms of scion infection (blossom, shoot or trauma blight) die each year once trees begin flowering; and that losses as high as 60 to 80 percent of the trees in a young orchard over a two year period have been observed more than once in several locations.

Rootstock Blight, yet another phase of Fire Blight, has been recognized recently and is associated primarily with highly susceptible rootstocks. On these trees, just a few blossom or shoot infections on the scion cultivar can supply bacteria that then move systemically into the rootstock where a canker can develop and eventually girdle the tree.

While the blighting of these rootstocks has been observed for many years, it was thought that the primary avenue for infections by the bacterium, *Erwinia amylovora*, was fairly direct through root suckers, cracks in the bark or insect injuries below the graft union. It is now known that the primary route of entry for the bacteria into the rootstock is internally, through otherwise healthy limbs and trunks from even a flow blossom or shot strikes on the scion variety. Once the bacteria reach a susceptible rootstock, they initiate the formation of new cankers that can completely girdle and kill the tree in one to a few months. Trees affected by rootstock blight generally show symptoms of decline and early death by mid to late season, but may not be apparent until the following spring. Where fire blight occurred the previous year in orchards grown on susceptible rootstocks, trees showing poor foliage color or dieback are usually removed from the orchard immediately and destroyed. Where highly susceptible apple rootstocks become infected, much of the scion trunk and major limbs above the graft union very typically remain symptomless, while a distinct dark brown canker develops around the rootstock. As this rootstock canker girdles the tree, the upper portion shows symptoms of general decline (poor foliage color, weak growth) by mid to late season. In some instances, the foliage of trees affected by rootstock blight develop early fall red color in late August to early September, not unlike that often associated with collar rot disease caused by a soilborne fungus. Some trees with rootstock infections may not show decline symptoms until the following spring, at which time cankers can be seen extending upward into the lower trunk.

The technology may also be used on other pathogenic organisms which are known to disrupt transpiration layers, within growing plant tissues, and ultimately bring death or limb loss to growing plants. Examples of these include organisms known to create the usually-lethal sub-surface plant diseases like: Oak Wilt, Dutch Elm Disease, Chestnut Blight, White Pine Rust, etc.

The invention will now be described in more detail by reference to the following examples. The only proper construction of these examples is as non-limiting illustrative examples showing various formulations, stabilities, and applications of the invention.

WORKING EXAMPLES

Example 1

Sub-surface Peracid Injections to Control Fire Blight

*Erwinia Amylovora*

The objective of this example was to evaluate prior known methods with the method of the present invention for control of a lethal plant pathogen—Fire Blight (*Erwinia amylovora*)—using a peroxygen compound (peracetic acid).

Table 1 and FIGS. 1–10 compare the results of utilizing a surface-bark treatment for control of the pathogen (as taught in the examples of GB 2187958 A, GB 2257630 A, or WO 94/06294) using peracetic acid wash solutions, versus an untreated control, and versus the method of the present invention of subsurface (hypo) cambium injections. The results demonstrate the significantly improved results of the present invention with all the infected orchard trees still living at the end of a growing season versus none of the control or prior art examples.

FIG. 1 exemplifies the results found while using the prior art surface peracid washes. Treatments as per the cited prior art examples using peracetic acid (POAA) concentrations of 3000–10,000 ppm active peracid had no effect on the disease. The results are typified by complete plant death occurring rapidly after the infection is first noticed. This is evidenced by blackening or darkening of the infected plant tissue, rapid spread of the infection zone (usually to the point of complete girdling of the limb or trunk, followed by desiccation and shriveling of any infected inner tissue beyond the microbial attack point, and finally by cracking and flaking of the dead area bark with concurrent death of all plant growth.

FIGS. 2–7 typify the present method of sub-surface cambium injections of peroxygen compounds to control the initial spread of the lethal blight. Instead of surface peroxygen treatments, as demonstrated in the prior art, the sub-surface injections of peracetic acid in and around the perimeter of the infection point stop the cambium layer destruction by the bacteria and, subsequently, stop the tree girdling and death. While various level of tissue destruction still occur (as seen in the FIGS. ) the cambium tissue and bark, though scarred, almost always remain intact and re-grow; i.e., the disease is controlled and the plants continue to live.

FIGS. 8–10 show the present method after 17 months beyond the exposure point to the disease. Again, the trees live and the pictures typify the results. As shown, the immediate infection point may or may not lose its attached bark area; however, plant death is not imminent from girdling and renewing scar tissue regrows around and in the infected area. Sometimes to the point that almost no observable tissue damage is noted and with some apparent recovery of cambium tissue in the infection zone. Most importantly, the trees have all returned to fruit production. These results are in sharp contrast to the prior art surface washing methods noted in WO 94/06294, GB 2257630 A, or GB 2187958.

TABLE 1

Various Oxidative Treatments to Control Fire Blight in Fruit Trees Comparing the Prior and Present Methods

| Treatment Condition | Tree Specie | Initial # of Plants Infected[1] (*E. amylovora*) | Living % (post 30 days)[2] | Field Trial Results (7 months) |
|---|---|---|---|---|
| Control Study |  |  |  |  |
| No oxidant treatment, only pruning[3] | Apple (Malus) | 6 trees | 0 | All trees are dead |
|  | Pear (Pyrus) | 2 trees | 0 | All trees are dead |

TABLE 1-continued

Various Oxidative Treatments to Control Fire Blight in Fruit Trees Comparing the Prior and Present Methods

| Treatment Condition | Tree Specie | Initial # of Plants Infected[1] (E. amylovora) | Living % (post 30 days)[2] | Field Trial Results (7 months) |
|---|---|---|---|---|
| Prior Art Treatments | | | | |
| WO 94/96294, GB 22576730 A, or GB 2187958 A POAA surface treated[4] | Apple (Malus) | 30 trees | 0 | All trees are dead |
| | Apricot (Prunus) | 2 trees | 0 | All trees are dead |
| | Pear (Pyrus) | 2 trees | 0 | All trees are dead |
| | Cherry (Prunus) | 1 tree | 0 | The tree is dead |
| | Crab Apple (Malus) | 1 tree | 0 | The tree is dead |
| Examples | | | | |
| POAA sub-surface treated[5] | Apple (Malus) | 5 trees | 100 | All trees are alive |
| | Apricot (Prunus) | 4 trees | 100 | All trees are alive |
| | Pear (Pyrus) | 5 trees | 100 | All trees are alive |

[1]Natural environment infection occurring within the production orchard
[2]The percentage of trees still living within each tree specie living 30 days after the initial Fire Blight infection time.
[3]Control study where no chemical applications were done to control the Fire Blight once the tree was infected.
[4]Peracid surface-bark treatments as per the cited prior art examples using peracetic acid (POAA) concentrations of 3000–10,000 ppm active peracid.
[5]Peracid acid (POAA) sub-surface cambium treatments using peracetic concentrations of 3000–5000 ppm active peracid.

Example 2

Oxidant Effects on Growing Plant Tissue

The objective of this example was to evaluate the effect of the peroxygen treatment, versus another oxidant (sodium hypochlorite—NaOCl), on growing plant tissue. Growing tissue from grape vines (vitis), apricot (prunus), and serviceberry (amelanchier) were subjected to treatments of 2000 ppm NaOCl and the tissue growth results noticed over time. In contrast to the peracid treatments described in Example 1, the sodium hypochlorite application caused complete tissue death with loss of tissue matter after about 1 week.

Also, it was found that injection of peracids into cambium layers can allow for migration of the peroxygen antimicrobial agent through the plant tissue. This result was evidenced by the movement of injected peracid through growing plant tissue over time. The experiment was conducted on a healthy apple tree by injection of peracetic acid into the cambium tissue. Thirty minutes later the peracid was detected two inches above the injection point. No tissue death was noted in this treated area over the remaining growing season.

The above specification, examples and data provide a complete description of the manufacture and use of the composition of the invention. Since many embodiments of the invention can be made without departing from the spirit and scope of the invention, the invention resides in the claims hereinafter appended.

We claim:

1. A method of protecting a growing plant from plant pathogens comprising injecting into an active transpiration layer of said plant a dilute aqueous solution comprising an effective amount of a water soluble peroxygen compound wherein the water soluble peroxygen compound is one or more $C_2$–$C_{12}$ peroxycarboxylic acids or a mixture of hydrogen peroxide and one or more $C_2$–$C_{12}$ peroxycarboxylic acids.

2. The method of claim 1, wherein the plant is a tree.

3. The method of claim 1, wherein the peroxygen compound is peroxyacetic acid.

4. The method of claim 1, wherein the peroxygen compound is a mixture of hydrogen peroxide and peroxyacetic acid.

5. The method of claim 1, wherein the peroxygen compound is a mixture of a $C_2$–$C_4$ peroxycarboxylic acid and a $C_5$–$C_{12}$ aliphatic peroxycarboxylic acid.

6. The method of claim 1, wherein the peroxygen compound is a mixture of a $C_2$–$C_4$ peroxycarboxylic acid and a $C_8$–$C_{12}$ aliphatic peroxycarboxylic acid.

7. The method of claim 6, wherein the peroxygen compound is a mixture of peroxyacetic acid and peroxyoctanoic acid.

8. The method of claim 1, wherein the dilute aqueous solution comprises an equilibrium combination of hydrogen peroxide, a $C_2$–$C_{12}$ peroxycarboxylic acid and a corresponding carboxylic acid; or an equilibrium combination of hydrogen peroxide, a mixture of a $C_2$–$C_4$ peroxycarboxylic acid and a $C_5$–$C_{12}$ aliphatic peroxycarboxylic acid and a corresponding carboxylic acid mixture thereof.

9. The method of claim 1, wherein the aqueous solution comprises at least about 100 parts per million (ppm) of said peroxygen compound.

10. The method of claim 9, wherein the peroxygen compound is peroxyacetic acid.

11. The method of claim 1, wherein the aqueous solution comprises:

(a) at least about 45 parts per million (ppm) of a $C_2$–$C_4$ peroxycarboxylic acid; and (b) at least about 5 parts per million (ppm) of a $C_5$–$C_{12}$ aliphatic peroxycarboxylic acid.

12. The method of claim 11, wherein said $C_2$–$C_4$ peroxycarboxylic acid is peroxyacetic acid.

13. The method of claim 11, wherein said $C_5$–$C_{12}$ aliphatic peroxycarboxylic acid is peroxyoctanoic acid.

14. The method of claim 1, wherein the plant pathogen is an organism which causes the plant diseases of Fire Blight, Oak Wilt, Dutch Elm Disease, Chestnut Blight, or White Pine Rust.

15. A method of treating a growing plant having an active transpiration layer to reduce the effect of plant pathogens on or in the growing plant, the method comprising:

(a) forming a passageway into the cambium layer of a growing plant; and (b) applying through the passageway an effective plant treating amount of a water peroxygen compound for sufficient period of time to reduce the undesirable effects of a plant pathogen on the plant life, wherein the water soluble peroxygen compound is one or more $C_2$–$C_{12}$ peroxycarboxylic acids or a mixture of hydrogen peroxide and one or more $C_2$–$C_{12}$ peroxycarboxylic acids.

16. The method of claim 15, wherein the plant comprises a tree.

17. The method of claim 15, wherein the peroxygen compound is peroxyacetic acid.

18. The method of claim 15, wherein the $C_2$–$C_{12}$ peroxycarboxylic acid is peroxyacetic acid.

19. The method of claim 15, wherein the peroxygen compound comprises a mixture of a $C_2$–$C_4$ peroxycarboxylic acid and a $C_5$–$C_{12}$ aliphatic peroxycarboxylic acid.

20. The method of claim 19, wherein said $C_2$–$C_4$ peroxycarboxylic acid is peroxyacetic acid, and said $C_5$–$C_{12}$ aliphatic peroxycarboxylic acid is peroxyoctanoic acid.

21. The method of claim 15, wherein the peroxygen compound comprises an equilibrium combination of hydrogen peroxide, a $C_2$–$C_{12}$ peroxycarboxylic acid and a corresponding carboxylic acid; or an equilibrium combination of hydrogen peroxide, a mixture of a $C_2$–$C_4$ peroxycarboxylic acid and a $C_5$–$C_{12}$ aliphatic peroxycarboxylic acid and a corresponding carboxylic acid mixture thereof.

22. The method of claim 15, wherein the plant pathogen is an organism which causes the plant diseases of Fire Blight, Oak Wilt, Dutch Elm Disease, Chestnut Blight, or White Pine Rust.

* * * * *